United States Patent [19]

O'Lenick, Jr.

[11] Patent Number: 6,060,619
[45] Date of Patent: May 9, 2000

[54] SILICONE LACTYLATES

[75] Inventor: Anthony J. O'Lenick, Jr., Dacula, Ga.

[73] Assignee: Lambent Technologies Inc., Norcross, Ga.

[21] Appl. No.: 09/188,486

[22] Filed: Nov. 9, 1998

[51] Int. Cl.[7] ..................................................... C07F 7/08
[52] U.S. Cl. ............................................................ 556/437
[58] Field of Search ............................................. 556/437

[56] References Cited

U.S. PATENT DOCUMENTS

| | | |
|---|---|---|
| 4,146,548 | 3/1979 | Forsythe . |
| 5,248,783 | 9/1993 | O'Lenick ................................ 548/110 |
| 5,296,625 | 3/1994 | O'Lenick, Jr. et al. ................ 556/437 |
| 5,374,759 | 12/1994 | Imperante et al. ...................... 556/437 |

*Primary Examiner*—Paul F. Shaver

[57] ABSTRACT

The invention relates to a series of novel silicone lactylates useful as emulsifiers. This class of compounds are prepared by the reaction of a carboxy functional silicone with the hydroxyl group on lactic acid. The products provide unique surfactant properties, specifically emulsification properties for many oil phases.

The compounds are useful for preparation of ultra mild products for use personal care applications for skin, hair care and related applications.

3 Claims, No Drawings

SILICONE LACTYLATES

BACKGROUND OF THE INVENTION

1. Field of the Invention

The invention relates to a series of novel silicone lactylates and their application as emulsifiers for a variety of oil phases. This class of compounds are prepared by the reaction of a carboxy functional silicone and the hydroxyl group of lactic acid. The products provide unique surfactant properties, specifically emulsification properties for many oil phases.

The compounds are useful for preparation of ultra mild products for use personal care applications for skin, hair care and related applications.

2. Arts and Practices

Silicone compounds have been known to be active at the surface of cellulosic and synthetic fibers as well as paper. They are good nondurable lubricants and are very stable to oxidation, however, their high cost and lack of efficiency at low concentrations as well as low durability have made their acceptance in commercial products quite low.

Many oil phases, which are insoluble in water, are emulsified to provide milky white opaque liquids which are easily formulated into a variety of applications. One problem here is that in order to obtain the necessary emulsion stability, relatively high loadings of traditional fatty surfactants are added. This minimizes the amount of oil phase delivered to the hair and skin and affects the feel on the skin and hair.

Carboxy functional silicone compounds useful as raw materials in the practice of the present invention are known to those skilled in the art. U.S. Pat. No. 4,844,888 issued in 1989 to Zawadizki discloses the carboxy functional silicone compounds useful as raw materials in the preparation of the compounds of the present invention.

Fatty lactylates are also known. U.S. Pat. No. 3,883,669 to Tsen et al, teaches the method of making lactylate salts. The methodology includes a reaction of fatty acid with lactic acid. The methodology is directed toward fatty derived materials. The present invention is aimed at making silicone based materials that provide not only the emulsification properties, but also provide conditioning and softening properties to hair. These properties are lacking in traditional lactylates.

U.S. Pat. No. 4,146,548 to Forsythe, incorporated herein by reference, describes an improved method of preparation of lactylates.

OBJECT OF THE INVENTION

It is the object of the present invention to provide novel silicone lactylates. These compounds have unique surface active properties. The compounds of the present invention in addition to their surfactant properties, provide lubricity, and hydrophobicity when applied to hair and skin.

It is another objective of the invention to provide silicone lactylates which can be used in personal care, textile, and industrial formulations to render surfactant properties to personal care formulations.

SUMMARY OF THE INVENTION

The present invention relates to novel silicone lactylates. These materials are excellent additives for highly effective surface modifying finishes for fiber and textiles. The compounds of the present invention are substantive to cellulosic and synthetic fibers as well as metal surfaces and plastic polymers.

As will become clear from the disclosure, the compounds of the present invention while having silicone present in the molecule, have unique surfactant properties which can be tailored for specific applications. This property is a direct result of the structure.

Surface active silicone compounds perform a variety of functions which include, (a) surface tension reduction, (b) wetting and detergency, (c) micelle formation, (d) emulsifying (f) solubilization, (g) foaming and (g) foam stabilization. The silicone nature of the surfactant introduces three clear advantages, (1) the silicone surfactant is itself substantive, conditioning and provides gloss to the hair and skin, (2) the silicone emulsifier is ultra mild to the skin and eyes and finally, (3) the emulsion prepared with these unique emulsifiers deliver their oil phase completely and easily upon application to skin and hair. This attribute results in the ability to use very low levels of emulsifier to obtain maximum benefit from the oil phase chosen.

The compounds of this invention are the reaction of the above carboxylate with lactic acid. Lactic acid is a hydroxy acid conforming to the following structure;

$$HO-CH-(CH_3)-C(O)-OH$$

The reaction is as follows:

$$\text{Silicone} - (O)OH + HO-CH-(CH_3)-C(O)-OH$$

$$\rightarrow \text{Silicone} -O-C(O)O-CH-(CH_3)-C(O)-OH + \text{water}$$

The compounds of the present invention conform to the following structure;

$$A-\underset{R}{\overset{R}{\underset{|}{Si}}}-O-\left[\underset{R}{\overset{R}{\underset{|}{Si}}}-O\right]_m\left[\underset{Q-R^1}{\overset{R}{\underset{|}{Si}}}-O\right]_n\underset{R}{\overset{R}{\underset{|}{Si}}}-A$$

Wherein

R is $CH_3$;

$R^1$ is $-O-CH-(CH_3)_{-OH}$;

Q is a $-(CH_2)_c-C(O)-$;

c is an integer ranging from 3 to 17;

A is either $-R$ or $-Q-R^1$, m is an integer ranging from 1 to 200;

n is an integer ranging 0 to 10 when A is $-Q-R^1$, and an integer ranging from 1 to 10 when A is R.

The compounds of the present invention are prepared by the reaction of a carboxy functional silicone with the hydroxyl group of lactic acid. This makes a class of compounds called lactylates. If however, the carboxyl group of the lactic acid is reacted with the carboyxlic group of another fatty acid, lactates result.

The process used for the preparation of the compounds of the present invention comprises the esterification reaction of (a) a carboxy containing silicone compound conforming to the following structure;

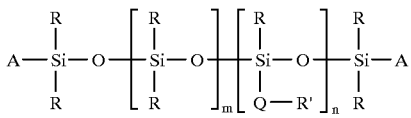

Wherein R is methyl;
R' is —OH;
Q is $(CH_2)_c$—C(O)—;
c is an integer from 3 to 17;
A is selected from the group consisting of methyl and —Q—R';
m is an integer ranging from 1 to 200;
n is an integer ranging 0 to 10 when A is —Q—$R^1$, and an integer ranging from 1 to 10 when A is R;
with
(b) an lactic acid; and optionally
(c) an esterification catalyst selected from the group consisting of sulfuric acid, tin salts, titanium salts and para toluene sulfonic acid.
said reaction to be carried out by reacting said carboxy functional silicone and said lactic acid in the presence of said catalyst, and heating to 150–250° C.

Preferred embodiments

In a preferred embodiment A is —R.
In another preferred embodiment A is —Q—$R^{1.}$

EXAMPLES

The compounds of the present invention are prepared by the reaction of a carboxy functional silicone compound and an alkylene oxide selected from the group consisting of ethylene oxide, propylene oxide and mixtures thereof. Examples of suitable reactants are as follows;

REACTANTS

Carboxy Functional Silicone Compounds

Many manufacturers offer a series of carboxy functional silicone compounds suitable for use as raw materials in the preparation of the esters of the present invention. These materials are marketed under the many trade names. Siltech Inc, and Dow Corning.

The preferred method of placing this type of reactive carboxy group into the silicone polymer is by the reaction of silanic hydrogen containing polymer with a terminal unsaturated carboxylate. This technology is well known to those skilled in the art.

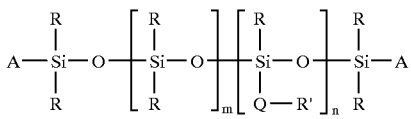

Wherein R is methyl;
R'is —OH;
Q is $(CH_2)_c$—C(O)—;
c is an integer from 3 to 17;
A is methyl;
m is an integer ranging from 1 to 200;
n is an integer ranging 0 to 10 when A is —Q—$R^1$, and an integer ranging from 1 to 10 when A is R;

| Example | Name | c | n | m |
|---|---|---|---|---|
| 1 | Siltech C 1000 | 10 | 3 | 15 |
| 2 | Siltech C 1100 | 10 | 1 | 20 |
| 3 | Siltech C 1200 | 3 | 4 | 50 |
| 4 | Siltech C 1300 | 3 | 2 | 200 |
| 5 | Siltech C 1400 | 4 | 1 | 29 |
| 6 | Siltech C 1500 | 17 | 3 | 1 |
| 7 | Siltech C 1600 | 17 | 4 | 150 |
| 8 | Siltech C 1700 | 4 | 10 | 55 |

Terminal Substituted Carboxy Functional Silicone

Terminal substituted carboxy functional silicone compounds are well known and are marketed in the trade under many names. The preferred method of placing this type of carboxyl group into the silicone polymer is by the reaction of terminal silanic hydrogen containing polymer with a terminal vinyl containing carboxy compound.

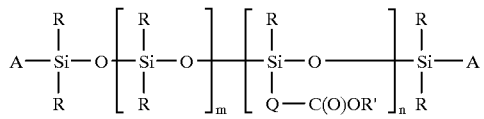

Wherein R is methyl;
R' is —H;
Q is $(CH_2)_c$—C(O)—O—;
c is an integer from 3 to 17;
n is 0;
A is —Q—R';

| Example | Name | c | m |
|---|---|---|---|
| 9 | Siltech CT 701 | 10 | 1 |
| 10 | Siltech CT 706 | 3 | 200 |
| 11 | Siltech CT 710 | 17 | 50 |
| 12 | Siltech CT 750 | 10 | 100 |
| 13 | Siltech CT 790 | 3 | 150 |

General Reaction Conditions

The esterification reaction is carried out by placing the required amount of the specified carboxy silicone into a suitable flask. Next is added 82.0 grams of lactic acid is added. The reaction can be carried out with out without catalyst. However catalyst is recommended to speed up the catalysts of choice are para toluene sulfonic acid, sulfuric acid and tin salts. We recommend 0.1% by weight of dibutyl tin dilaurate. The reaction mass is heated to 180–200° C. Water is distilled off. When 97% of the theoretical amount of water is distilled off, the reaction is stopped. The product is used without purification.

Example 14

General Procedure

The esterification reaction is carried out by placing the 608.0 grams of carboxy silicone example 1 into a suitable flask. Next is added 82.0 grams of lactic acid is added. The reaction can be carried out with out without catalyst. However catalyst is recommended to speed up the reaction. The catalysts of choice are para toluene sulfonic acid, sulfuric acid and tin salts. We recommend 0.1% by weight of dibutyl tin dilaurate. The reaction mass is heated to 180–200° C. Water is distilled off. When 97% of the theoretical amount of water is distilled off, the reaction is stopped. The product is used without purification.

EXAMPLE 15–25

Example 14 is repeated, only this time the specified amount of the specified carboxy functional silicone is used in place of the specified carboxy silicone (example 1).

| Example Number | Carboxy Silicone Example/grams | |
|---|---|---|
| 15 | 2 | 1827.0 |
| 16 | 3 | 1051.0 |
| 17 | 4 | 7570.0 |
| 18 | 5 | 2409.0 |
| 19 | 6 | 361.0 |
| 20 | 7 | 3100.0 |
| 21 | 8 | 524.2 |
| 22 | 9 | 290.0 |
| 23 | 10 | 7553.0 |
| 24 | 11 | 2200.0 |
| 25 | 12 | 4000.0 |

The compounds of the present invention can be tailored to allow for the emulsion of specific oil phases. This flexibility, the ability of the emulsifier to be incorporated into the emulsion at low concentrations and the fact that the silicone emulsifier has no affect upon skin feel are all very desirable attributes of the compounds of the present invention. They are unexpected advantages over the commonly used surfactants.

What is claimed:

1. A silicone compound which conforms to the following structure;

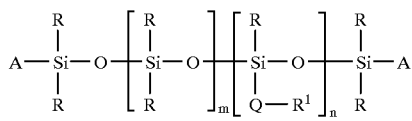

wherein

R is $CH_3$;

$R^1$ is —O—CH—$(CH_3)$—C(O)—OH

Q is a —$(CH_2)_c$—C(O)—;

c is an integer ranging from 3 to 17;

A is either —R or —Q—$R^1$, m is an integer ranging from 1 to 200;

n is an integer ranging 0 to 10 when A is —Q—$R^1$, and an integer ranging from 1 to 10 when A is R.

2. A silicone compound of claim 1 wherein A is —R.

3. A silicone compound of claim 1 wherein A is —Q—$R^1$.

* * * * *